(12) United States Patent
Nathanson (10) Patent No.: US 7,967,765 B2
(45) Date of Patent: Jun. 28, 2011

(54) ORTHOPEDIC BRACE SUSPENSION SYSTEM

(75) Inventor: Jeremy J. Nathanson, San Clemente, CA (US)

(73) Assignee: DJO, LLC, Vista, CA (US)

( * ) Notice: Subject to any disclaimer, the term of this patent is extended or adjusted under 35 U.S.C. 154(b) by 182 days.

(21) Appl. No.: 10/985,366

(22) Filed: Nov. 10, 2004

(65) Prior Publication Data

US 2005/0148918 A1    Jul. 7, 2005

Related U.S. Application Data (60) Provisional application No. 60/534,584, filed on Jan. 6, 2004, provisional application No. 60/557,149, filed on Mar. 29, 2004.

(51) Int. Cl.
*A61F 5/01* (2006.01)
(52) U.S. Cl. .............................. 602/5; 602/16; 602/23
(58) Field of Classification Search ............... 602/5, 16, 602/17, 19–21, 23–28, 36, 60–62, 65
See application file for complete search history.

(56) References Cited

U.S. PATENT DOCUMENTS

| | | | | |
|---|---|---|---|---|
| 2,270,685 A | * | 1/1942 | Miller | 602/62 |
| 3,046,981 A | * | 7/1962 | Biggs, Jr. et al. | 602/26 |
| 3,055,359 A | | 9/1962 | Palmer | |
| 3,093,131 A | * | 6/1963 | Kashyap | 602/23 |
| 3,350,719 A | | 11/1967 | McClure, Jr. | |
| 3,416,519 A | * | 12/1968 | Dowers | 602/23 |
| 3,958,569 A | | 5/1976 | Vosburgh | |
| 3,970,081 A | | 7/1976 | Applegate, Jr. | |
| 3,976,057 A | | 8/1976 | Barclay | |
| 3,993,056 A | | 11/1976 | Rabischong et al. | |
| 4,027,666 A | | 6/1977 | Marx | |
| 4,041,940 A | * | 8/1977 | Frankel et al. | 602/26 |
| 4,090,508 A | * | 5/1978 | Gaylord, Jr. | 602/26 |
| 4,169,467 A | | 10/1979 | Rabischong et al. | |
| 4,295,466 A | | 10/1981 | Prout | |
| 4,361,142 A | | 11/1982 | Lewis et al. | |
| 4,372,298 A | | 2/1983 | Lerman | |
| 4,407,496 A | | 10/1983 | Johnson | |
| 4,425,912 A | * | 1/1984 | Harper | 602/26 |

(Continued)

FOREIGN PATENT DOCUMENTS

DE        3 511 250        11/1985

(Continued)

OTHER PUBLICATIONS

FLA Orthopedics, Inc., Specter ROM & P-ROM Braces, magazine advertisement, 1 page, 1998.

(Continued)

*Primary Examiner* — Danton DeMille
(74) *Attorney, Agent, or Firm* — Ropes & Gray LLP (57) ABSTRACT

Provided are apparatus and methods of securing an orthopedic brace on a wearer such that the brace is unlikely to migrate. In preferred embodiments, the apparatus includes a band that extends entirely around the wearer, making contact with the entire circumference of the wearer. In certain embodiments, a strap secured to the brace threads through loops on the band, thereby operably connecting the brace and the band. In certain other embodiments, the apparatus further includes a belt that overlaps the band. Suspenders operably connect the brace to the band/belt. Because the band makes contact with the entire circumference of the wearer, the apparatus comfortably secures the brace to the wearer while effectively preventing migration of the brace and without hindering the intended function of the brace.

14 Claims, 10 Drawing Sheets

U.S. PATENT DOCUMENTS

| | | | |
|---|---|---|---|
| 4,436,099 A | 3/1984 | Raftopoulos | |
| 4,506,661 A | 3/1985 | Foster | |
| 4,556,053 A | 12/1985 | Irons | |
| 4,602,627 A | 7/1986 | Vito et al. | |
| 4,607,628 A | 8/1986 | Dashefsky | |
| 4,633,867 A | 1/1987 | Kausek et al. | |
| 4,643,176 A | 2/1987 | Mason et al. | |
| 4,651,722 A | 3/1987 | Karczewski | |
| 4,686,969 A | 8/1987 | Scott | |
| 4,697,583 A | 10/1987 | Mason et al. | |
| 4,718,665 A | 1/1988 | Airy et al. | |
| 4,732,143 A | 3/1988 | Kausek et al. | |
| 4,751,920 A | 6/1988 | Mauldin et al. | |
| 4,768,500 A | 9/1988 | Mason et al. | |
| 4,781,179 A | 11/1988 | Colbert | |
| 4,791,916 A | 12/1988 | Paez | |
| 4,796,610 A | 1/1989 | Cromartie | |
| 4,801,138 A | 1/1989 | Airy et al. | |
| 4,802,466 A | 2/1989 | Meyers et al. | |
| 4,803,975 A | 2/1989 | Meyers | |
| 4,805,606 A * | 2/1989 | McDavid, III | 602/26 |
| 4,817,588 A | 4/1989 | Bledsoe | |
| 4,838,251 A | 6/1989 | Chignon et al. | |
| 4,854,308 A | 8/1989 | Drillio | |
| 4,887,590 A | 12/1989 | Logue et al. | |
| 4,930,499 A * | 6/1990 | Rowe | 602/19 |
| 4,940,044 A | 7/1990 | Castillo | |
| 4,941,462 A | 7/1990 | Lindberg | |
| 4,955,369 A | 9/1990 | Bledsoe et al. | |
| 4,986,264 A | 1/1991 | Miller | |
| 5,000,169 A * | 3/1991 | Swicegood et al. | 602/16 |
| 5,002,045 A | 3/1991 | Spademan | |
| 5,022,391 A | 6/1991 | Weidenburner | |
| 5,025,782 A | 6/1991 | Salerno | |
| 5,052,379 A | 10/1991 | Airy et al. | |
| 5,058,574 A * | 10/1991 | Anderson et al. | 602/16 |
| 5,078,127 A | 1/1992 | Daneman et al. | |
| 5,085,210 A | 2/1992 | Smith, III | |
| 5,107,824 A | 4/1992 | Rogers et al. | |
| 5,135,469 A | 8/1992 | Castillo | |
| 5,224,924 A * | 7/1993 | Urso | 602/19 |
| 5,230,700 A | 7/1993 | Humbert et al. | |
| 5,267,946 A | 12/1993 | Singer et al. | |
| 5,277,697 A | 1/1994 | France et al. | |
| 5,277,698 A | 1/1994 | Taylor | |
| 5,302,169 A | 4/1994 | Taylor | |
| 5,306,230 A * | 4/1994 | Bodine | 602/26 |
| 5,328,446 A * | 7/1994 | Bunnell et al. | 602/16 |
| 5,334,135 A | 8/1994 | Grim et al. | |
| 5,358,469 A | 10/1994 | Patchel et al. | |
| 5,372,575 A | 12/1994 | Sebastian | |
| 5,385,538 A | 1/1995 | Mann | |
| 5,400,806 A | 3/1995 | Taylor | |
| 5,433,699 A | 7/1995 | Smith, III | |
| 5,437,619 A | 8/1995 | Malewicz et al. | |
| 5,457,891 A | 10/1995 | Taylor | |
| 5,458,565 A | 10/1995 | Tillinghast, III et al. | |
| 5,462,517 A | 10/1995 | Mann | |
| 5,558,627 A | 9/1996 | Singer et al. | |
| 5,562,605 A | 10/1996 | Taylor | |
| 5,586,970 A | 12/1996 | Morris et al. | |
| 5,599,288 A | 2/1997 | Shirley et al. | |
| 5,626,557 A | 5/1997 | Mann | |
| 5,649,901 A | 7/1997 | DiPietro et al. | |
| 5,658,241 A | 8/1997 | Deharde et al. | |
| 5,658,244 A | 8/1997 | Townsend et al. | |
| 5,672,152 A | 9/1997 | Mason et al. | |
| 5,741,220 A | 4/1998 | Brink | |
| 5,749,840 A | 5/1998 | Mitchell et al. | |
| 5,782,780 A | 7/1998 | Mason et al. | |
| 5,797,864 A * | 8/1998 | Taylor | 602/26 |
| 5,857,989 A | 1/1999 | Smith, III | |
| 5,865,775 A | 2/1999 | Peoples et al. | |
| 5,943,705 A | 8/1999 | Sink | |
| 5,980,435 A | 11/1999 | Joutras et al. | |
| 6,001,074 A | 12/1999 | Kenney | |
| 6,045,521 A | 4/2000 | Saitoh et al. | |
| 6,110,138 A * | 8/2000 | Shirley | 602/26 |
| RE37,209 E | 6/2001 | Hensley et al. | |
| 6,336,909 B2 * | 1/2002 | Gildersleeve et al. | 602/26 |
| 6,387,066 B1 | 5/2002 | Whiteside | |
| 6,428,495 B1 | 8/2002 | Lynott | |
| 6,478,758 B1 | 11/2002 | Hassler | |
| 6,478,760 B2 | 11/2002 | Darcey | |
| 6,485,448 B2 | 11/2002 | Lamping et al. | |
| 6,623,439 B2 | 9/2003 | Nelson et al. | |
| 6,641,549 B2 * | 11/2003 | Darcey | 602/8 |
| 6,793,641 B2 | 9/2004 | Freeman et al. | |
| 7,156,818 B2 * | 1/2007 | Salmon et al. | 602/5 |
| 2002/0183672 A1 | 12/2002 | Enzerink et al. | |
| 2004/0167452 A1 | 8/2004 | Mason et al. | |

FOREIGN PATENT DOCUMENTS

| | | |
|---|---|---|
| EP | 0 290 409 | 11/1988 |
| JP | 6380 | 6/1903 |
| JP | 2000197654 | 7/2000 |
| WO | WO 86/04228 | 7/1986 |
| WO | WO 90/09157 | 8/1990 |
| WO | WO 95/25489 | 9/1995 |
| WO | WO 98/14144 | 4/1998 |
| WO | WO 03/103546 | 12/2003 |

OTHER PUBLICATIONS

Townsend Design, Functional Knee Bracing Solutions-Specialty Braces internet article at http://townsenddesign.com/specialty.html, 2003.

* cited by examiner

ORTHOPEDIC BRACE SUSPENSION SYSTEM

RELATED APPLICATIONS

This application claims priority to provisional application Ser. No. 60/534,584, filed on Jan. 6, 2004, and to provisional application Ser. No. 60/557,149, filed on Mar. 29, 2004. The entire contents of each of these applications are hereby expressly incorporated by reference.

BACKGROUND OF THE INVENTION

1. Field of the Invention

The present invention relates to orthopedic braces.

2. Description of the Related Art

Figure 1:
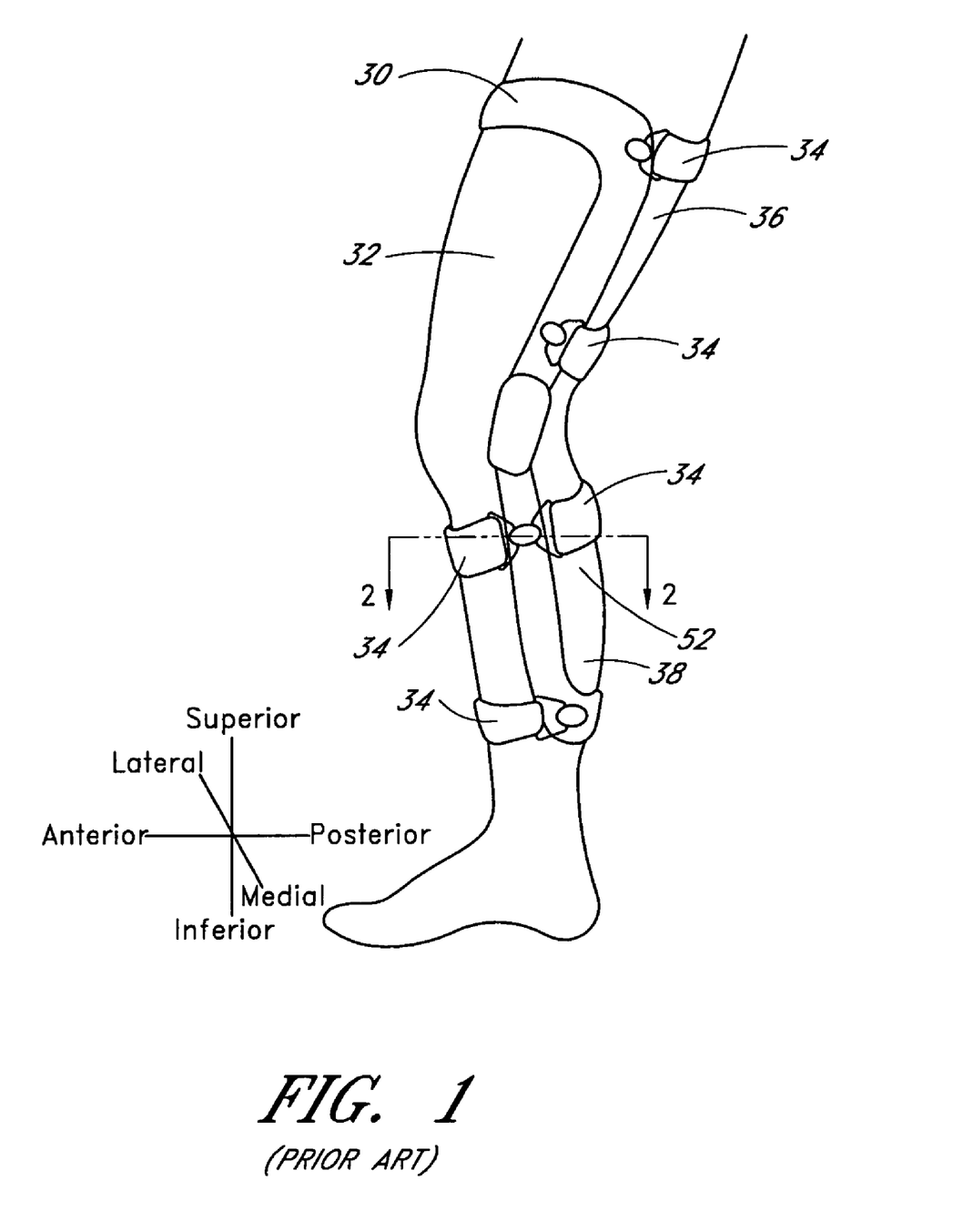
FIG. 1 is a left-side elevational view of a prior art orthopedic knee brace secured to a wearer's leg.

FIG. 1 illustrates a conventional orthopedic knee brace 30. Such braces tend to slide downward on the wearer's leg 32. A few different factors cause this downward migration. First, when the wearer is standing or sitting gravity tends to pull the brace 30 downward along the wearer's leg 32. When the wearer walks or runs, the added acceleration of the wearer's gait exacerbates the downward pull of gravity upon the brace 30.

Second, like the illustrated brace 30 most knee braces are secured to the wearer's leg 32 with straps 34. These straps 34 generate friction on the leg 32 by applying a compressive force to the leg 32. But the human leg 32 has a generally conical shape, being wider at the thigh 36 and narrower at the calf 38. As a result, the compressive force applied by each strap 34 tends to make the strap 34 slide downward. Further, the conical shape provides no resistance to the natural tendency of the brace 30 to slide downward under the influence of gravity.

Figure 2:
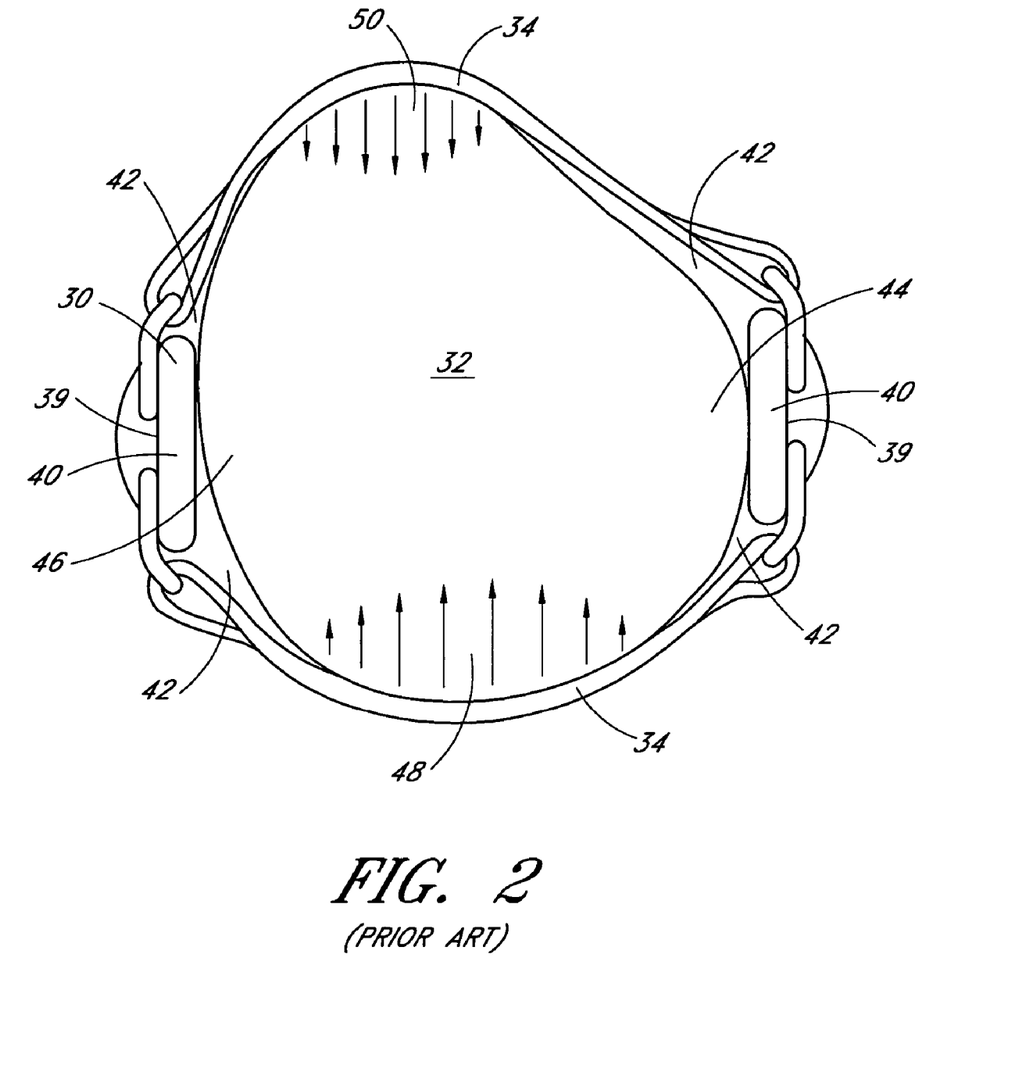
FIG. 2 is a cross-sectional view of the brace and leg of FIG. 1, taken along the line 2-2 in FIG. 1.

Third, conventional straps 34 do not contact the wearer's leg 32 at all points around the perimeter. As FIG. 2 illustrates, ends of the straps 34 attach to outward facing surfaces 39 of rigid frame portions 40 of the brace 30. The outward facing surfaces 39 of the frame portions 40 are spaced from the wearer's leg 32. This spacing creates gaps 42 between the straps 34 and the medial regions 44 and lateral regions 46 of the wearer's leg 32, where the straps 34 connect to the frame 40. The gaps 42 create uneven pressure on the leg 32, with pressure points at the anterior regions 48 and posterior regions 50. The arrows in FIG. 2 represent the pressure applied by the straps 34, with the magnitude of the pressure being directly proportional to the length of the arrow. The pressure points and gaps 42 contribute to wearer discomfort and the tendency for the straps 34 to slide down the leg 32.

To combat downward migration, some knee braces include a strap that resides on the top of the wearer's gastroc muscle 52 (FIG. 1). For example, the brace 30 illustrated in FIG. 1 includes such an anti-migration strap 34. FIGS. 9-12 of U.S. Pat. No. 4,643,176 also disclose an anti-migration strap 60. The strap 60 is constructed of a flexible but substantially non-stretchable material. The strap 60 wraps around the wearer's leg where the calf flares outwardly immediately below the knee joint.

Figure 3:
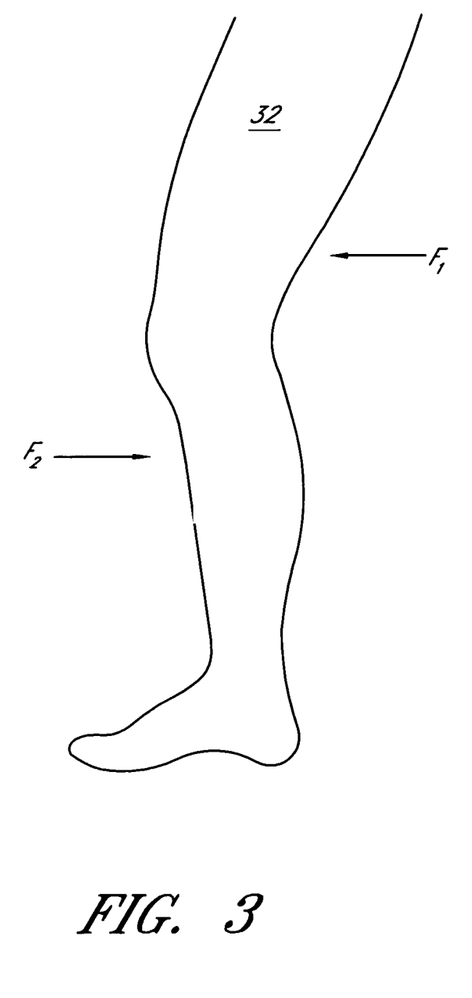
FIG. 3 is a left-side elevational view of a leg, illustrating the shear forces that a knee brace should apply to the leg in order to simulate the action of the ACL.
Figure 4:
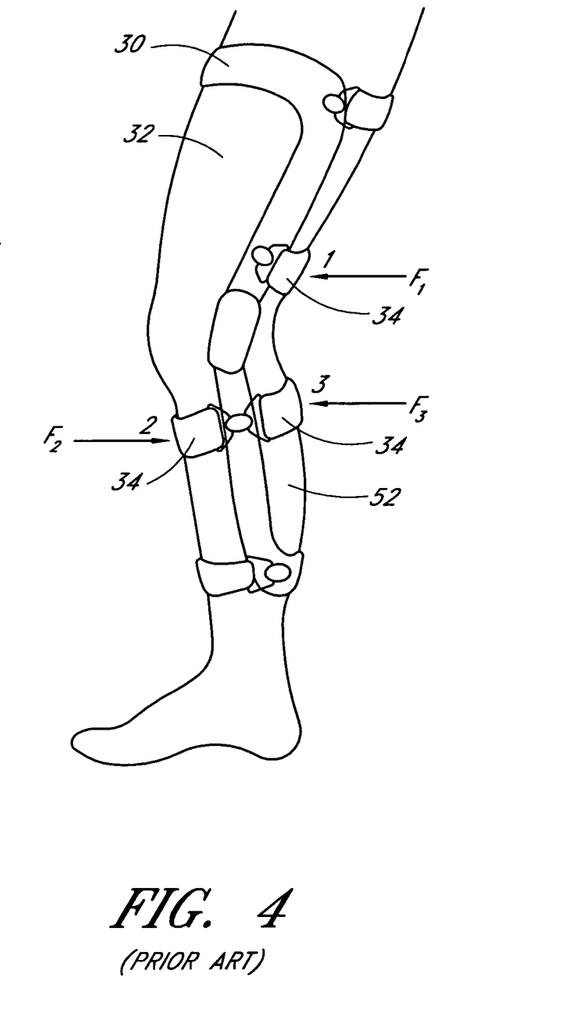
FIG. 4 is a left-side elevational view of the brace and leg of FIG. 1, illustrating the shear forces applied to the knee by the straps most proximal to the knee.

In certain knee braces, particularly those knee braces that treat and/or prevent injuries to the wearer's anterior cruciate ligament (ACL), an anti-migration strap atop the gastroc muscle can hinder the intended beneficial function of the orthosis. FIG. 3 illustrates the shear forces $F_1$, $F_2$ that a knee brace should apply to a wearer's leg 32 in order to simulate the action of the ACL (see, for example, U.S. Pat. No. 4,697,583). FIG. 4 illustrates an ACL brace 30 including an anti-migration strap 34 atop the gastroc muscle 52. FIG. 4 further illustrates the direction of each force $F_1$, $F_2$, $F_3$ applied by each strap 1, 2, 3. The straps 1, 2 apply beneficial forces $F_1$, $F_2$, while the strap 3 applies a force $F_3$ that opposes the force $F_2$ applied by the strap 2.

A system for comfortably fitting an orthopedic brace to a wearer's limb while effectively preventing migration of the brace and without hindering the intended function of the brace would be of great benefit to those who wear orthopedic braces.

SUMMARY OF THE INVENTION

The preferred embodiments of the present orthopedic brace suspension system have several features, no single one of which is solely responsible for their desirable attributes. Without limiting the scope of this orthopedic brace suspension system as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include effective brace fixation on the wearer's leg with minimal or no brace migration and minimal or no detraction from the intended function of the brace.

One embodiment of the present orthopedic brace suspension system comprises an orthopedic brace including first and second rigid uprights and at least one strap. The system further comprises a band that is adapted to extend around a wearer. The band includes at least one loop that extends transversely across the band. When the brace is worn, the at least one strap threads through the at least one loop.

Another embodiment of the present orthopedic brace suspension system comprises an orthopedic brace including first and second rigid uprights. The system further comprises a band that is adapted to extend around the wearer. The band includes at least one loop that extends transversely across the band. The system further comprises a belt that is adapted to extend around the wearer, overlapping the band and threading through the at least one loop. The system further comprises at least one suspender. When the brace is worn, the at least one suspender operably connects the belt to one of the first and second rigid uprights.

Another embodiment of the present orthopedic brace suspension system comprises an orthopedic brace including first and second rigid uprights. The system further comprises a band that is adapted to extend around a limb of a wearer such that the band contacts the entire circumference of the limb. When the brace is worn, the brace is operably connected to the band.

Another embodiment of the present orthopedic brace suspension system comprises a method of securing an orthopedic brace to a wearer. The method comprises the step of applying to the wearer a band of material. The band includes at least one loop that extends transversely across the band. The band contacts the entire circumference of the wearer. The method further comprises the step of threading a strap of the brace through the at least one loop.

Another embodiment of the present orthopedic brace suspension system comprises a method of securing an orthopedic brace to a wearer. The method comprises the step of applying to the wearer a band of material. The band contacts the entire circumference of the wearer. The method further comprises the step of applying to the wearer a belt of material.

The belt overlaps the band. The method further comprises the step of connecting at least one suspender between the brace and the belt.

BRIEF DESCRIPTION OF THE DRAWINGS

The preferred embodiments of the present orthopedic brace suspension system, illustrating its features, will now be discussed in detail. These embodiments depict the novel and non-obvious orthopedic brace suspension system shown in the accompanying drawings, which are for illustrative purposes only. These drawings include the following figures, in which like numerals indicate like parts.

DETAILED DESCRIPTION OF THE PREFERRED EMBODIMENTS

With reference to FIG. 1, the following directional terms will be used in this application. Anterior denotes toward the front of the wearer. Posterior denotes toward the rear of the wearer. Superior denotes higher on the wearer. Inferior denotes lower on the wearer. Medial denotes toward a vertical centerline of the wearer. Lateral denotes away from a vertical centerline of the wearer.

Figure 5:
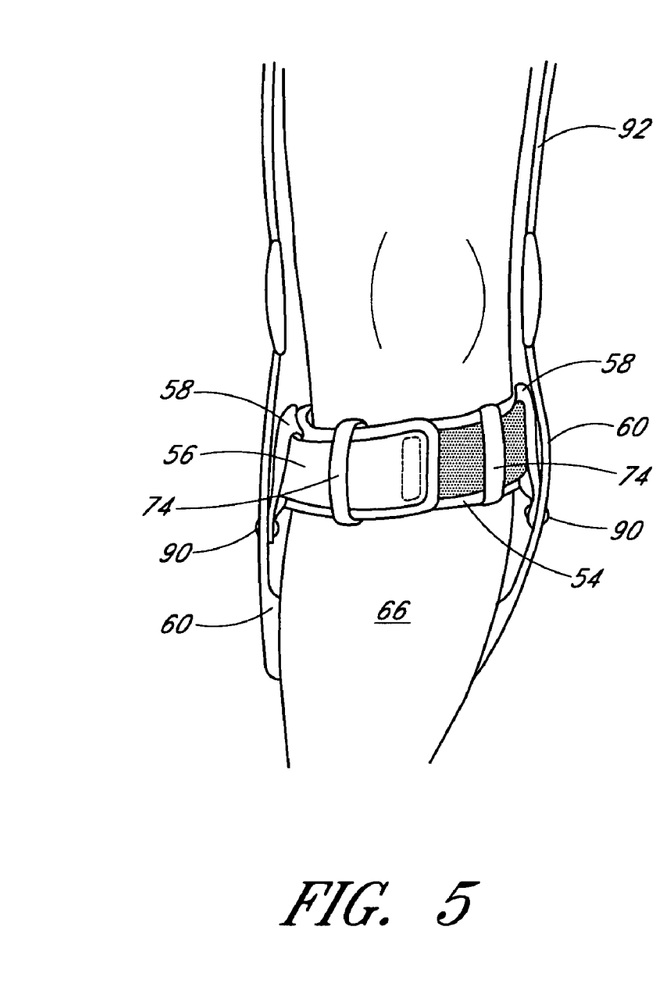
FIG. 5 is a front elevational view of one embodiment of the present orthopedic brace suspension system secured to a wearer's leg.
Figure 6:
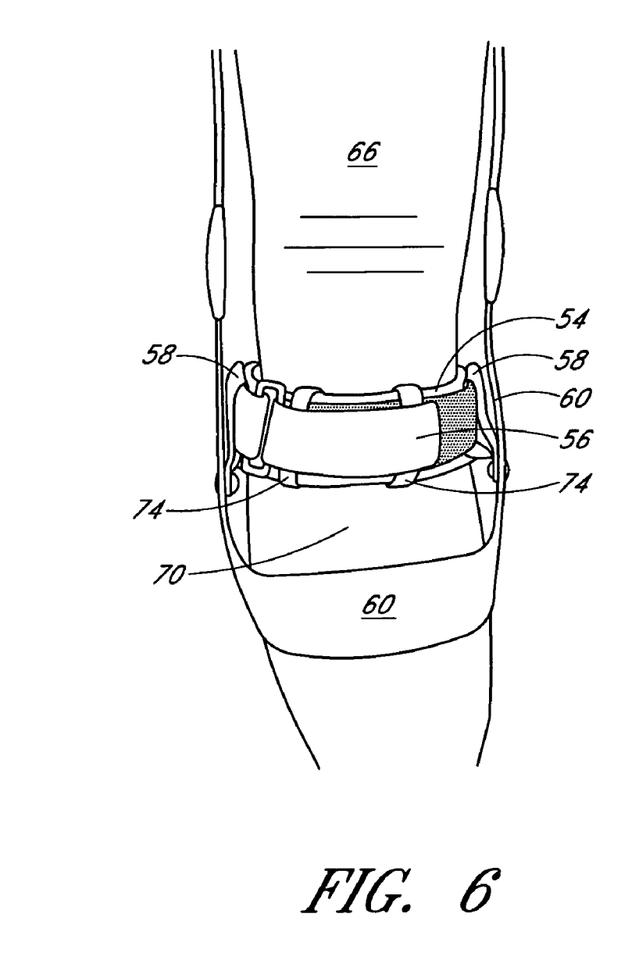
FIG. 6 is a rear elevational view of the orthopedic brace suspension system and leg of FIG. 5.
Figure 8:
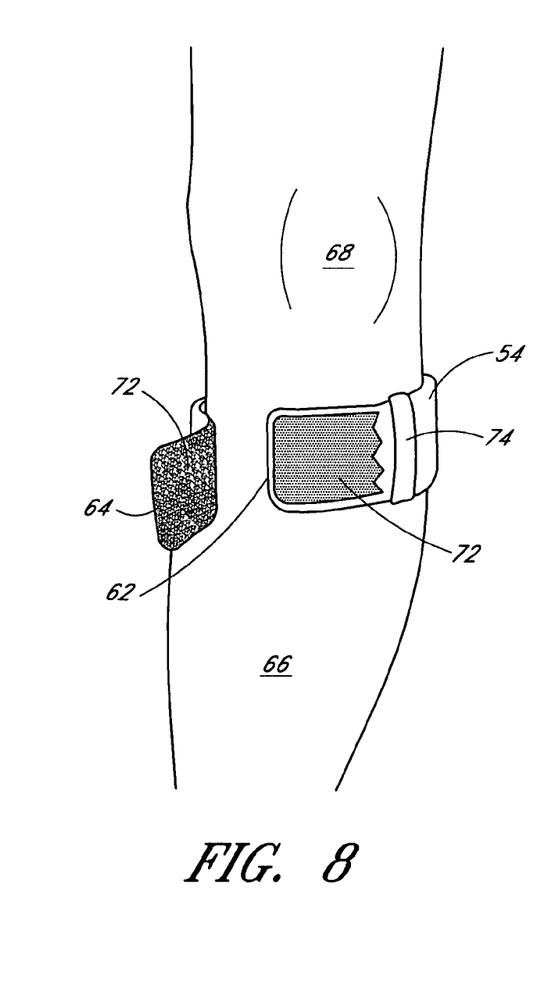
FIG. 8 is a front elevational view of one embodiment of the inner band of the system of FIG. 5, illustrating the band applied to a wearer's leg.
Figure 9:
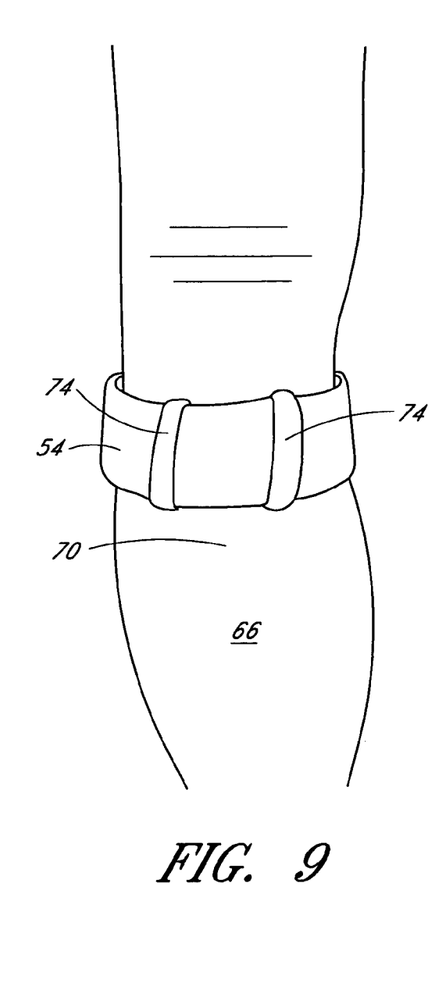
FIG. 9 is a rear elevational view of the inner band and the leg of FIG. 8.
Figure 10:
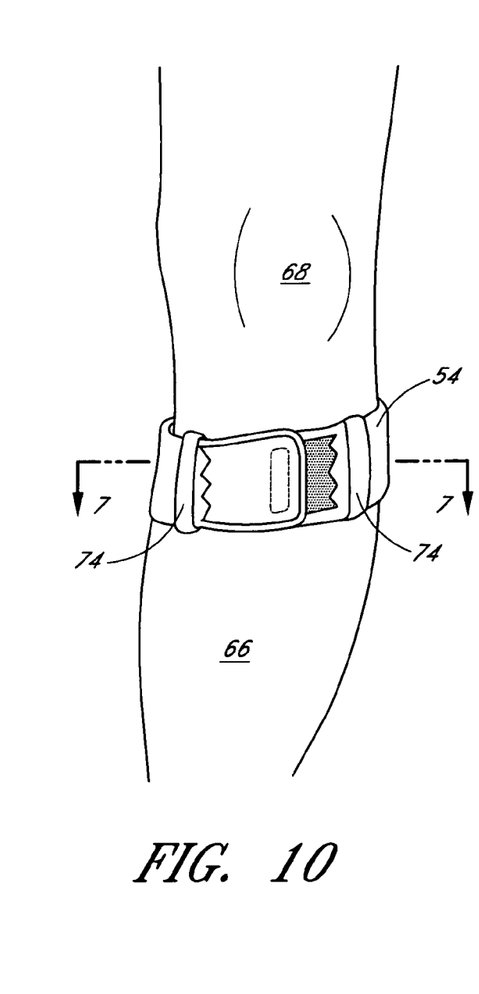
FIG. 10 is a front elevational view of the inner band and the leg of FIG. 8.

FIGS. 5-15 illustrate one embodiment of the present orthopedic brace suspension system. With reference to FIGS. 5 and 6, this embodiment includes three main parts: an inner band 54, an outer belt 56, and suspenders 58 connecting the belt 56 to the rigid brace frame 60. With reference to FIGS. 8-10, the inner band 54 comprises an elongate strip of material including a first end 62 and a second end 64. The inner band 54 extends around the entire circumference of the wearer's leg 66 just below the patella 68 (FIG. 10), and just above the gastroc muscle 70 (FIG. 9). The inner band 54 is preferably constructed of an elastic material that is comfortable to wear directly against the skin. Examples of such materials are neoprene and DRYTEX®. Of course, as those of skill in the art will appreciate, the wearer need not wear the inner band 54 directly against his or her skin, and could, for example, fasten the band 54 over a layer of clothing. Those of skill in the art will further appreciate that the inner band 54 need not include first and second ends 62, 64. The inner band 54 could, for example, comprise a continuous loop that the wearer positions on his or her leg by sliding it up and over the foot and ankle.

Figure 7:
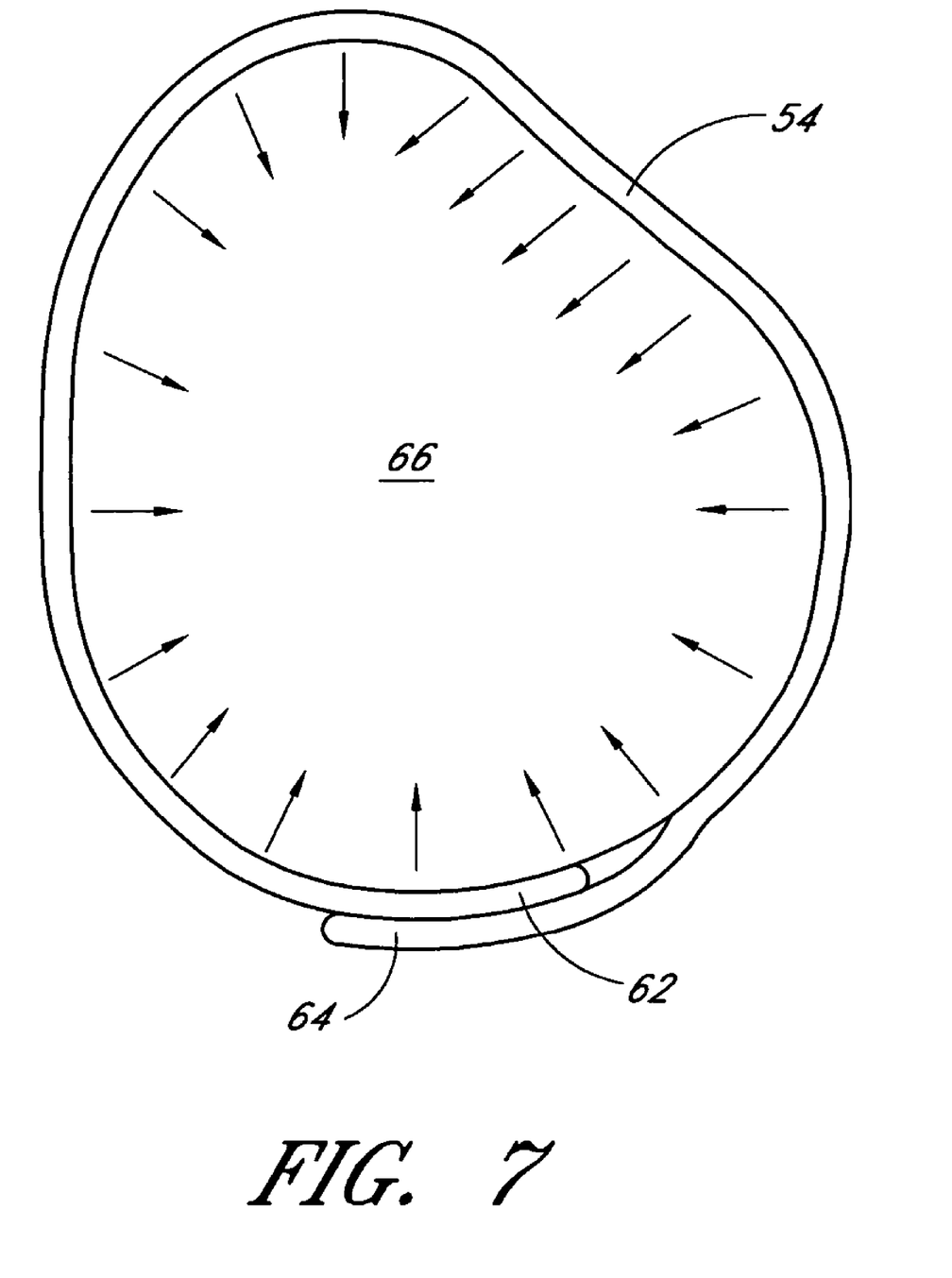
FIG. 7 is a schematic cross-sectional view of the system and leg of FIG. 5, taken along the line 7-7 in FIG. 5.

The first and second ends 62, 64 of the band meet beneath the wearer's patella 68 (FIGS. 8 and 10). The ends 62, 64 preferably include mating fasteners 72, such as hook-and-loop material. Those of skill in the art will appreciate that other types of fasteners, such as buttons or snaps, could be used instead. The wearer secures the band 54 to his or her leg 66 by positioning the first end 62 beneath the patella 68 with the fastener 72 facing out. The wearer then wraps the second end 64 around the back of his or her leg 66 and secures the fastener 72 on the second end 64 to the mating fastener 72 on the first end 62. Of course, the first and second ends 62, 64 of the band 54 need not be positioned anteriorly of the wearer. The band 54 could be rotated about the wearer's leg 66 so that the first and second ends 62, 64 are positioned anywhere around the leg 66. The band 54 preferably fits snug, but not so tight as to restrict circulation. The elasticity of the band 54 advantageously allows the band 54 to contact the entire circumference of the wearer's leg 66, as illustrated in FIG. 7. The elasticity of the band 54 also advantageously allows the band 54 to stretch to fit a range of leg circumferences without bunching up.

With reference to FIGS. 8-10, the band 54 includes a plurality of loops 74 that extend in a transverse direction across the band 54. In the illustrated embodiment, the band 54 includes four such loops 74, with two loops 74 being positioned on an anterior portion of the band 54 (FIG. 10), and two loops 74 being positioned on a posterior portion of the band 54 (FIG. 9). Those of skill in the art will appreciate that the band 54 could include virtually any number of loops 74, and that they could be positioned anywhere on the band 54. The loops 74 are preferably secured in place on the band 54, for example with stitching (not shown), such that they cannot slide along the length of the band 54. The loops 74 could, however, be freely slidable along the length of the band 54.

Figure 11:
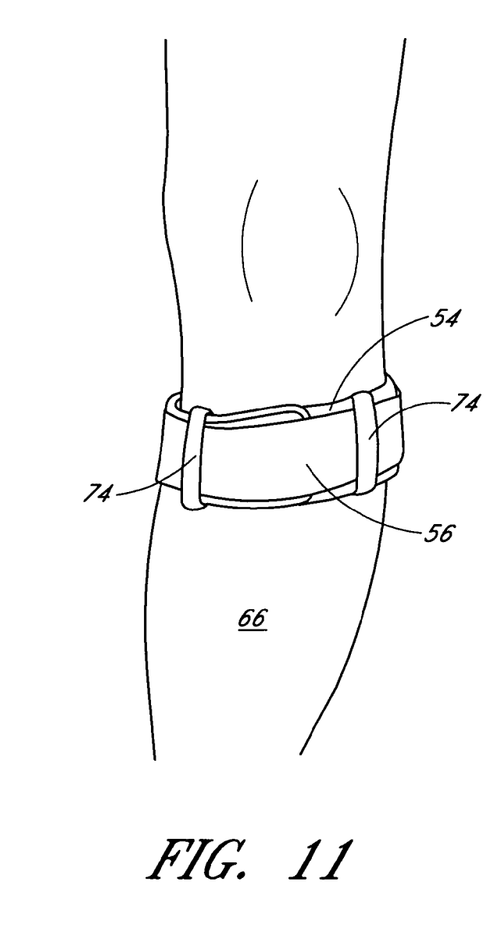
FIG. 11 is a front elevational view of the inner band and the leg of FIG. 8, and one embodiment of the outer belt of the system of FIG. 5, illustrating the belt applied over the band.
Figure 12:
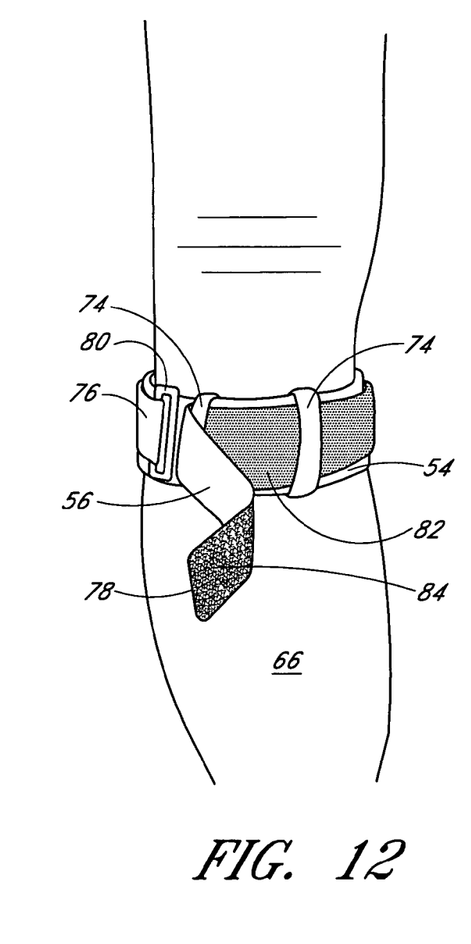
FIG. 12 is a rear elevational view of the inner band, leg and outer belt of FIG. 11.
Figure 13:
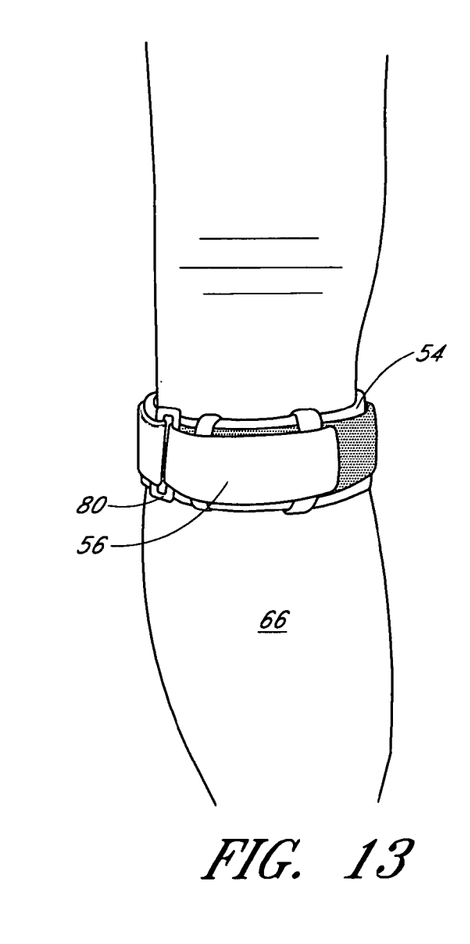
FIG. 13 is a rear elevational view of the inner band, leg and outer belt of FIG. 11.

With reference to FIGS. 11-13, the outer belt 56 comprises an elongate strip of material including a first end 76 and a second end 78 (FIG. 12). The belt 56 is preferably constructed of an inelastic material, such as nylon. The outer belt 56 extends around the wearer's leg 66, overlapping the inner band 54 and threading through the loops 74 on the inner band 54. The first end 76 of the belt includes an attached D-ring 80. The D-ring 80 is preferably constructed of a metal, such as steel. The D-ring 80 could, however, be constructed of virtually any sturdy material, such as plastic or composite.

At least part of an outward facing surface 82 (FIG. 12) of the belt 56 is preferably covered with either the hook portion or the loop portion of a hook-and-loop material. At least part of an inward facing surface 84 of the second end 78 of the belt 56 preferably includes the mating portion of a hook-and-loop material. The second end 78 threads through the D-ring 80 on the first end 76 and folds back over onto the outward facing surface 82 of the belt 56. The hook-and-loop material on the second end 78 mates with the hook-and-loop material on the outward facing surface 82. The wearer preferably pulls the belt 56 snug before securing the second end 78 to the outward facing surface 82. The first end 76 of the belt 56, adjacent the D-ring 80, may be permanently secured to the inner band 54, as by stitching (not shown).

Figure 14:
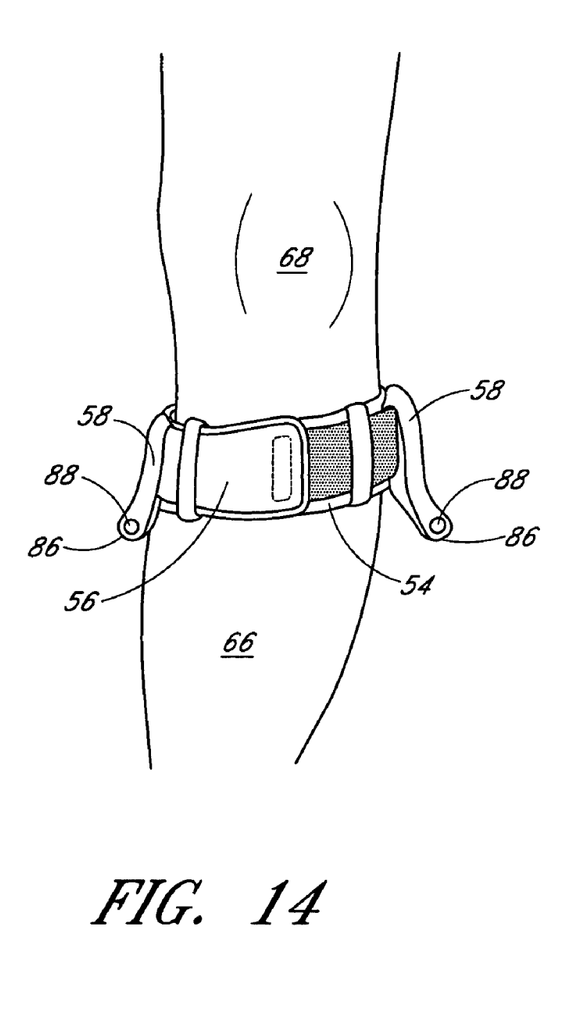
FIG. 14 is a front elevational view of the inner band, leg and outer belt of FIG. 11, and one embodiment of the suspenders of the system of FIG. 5.
Figure 15:
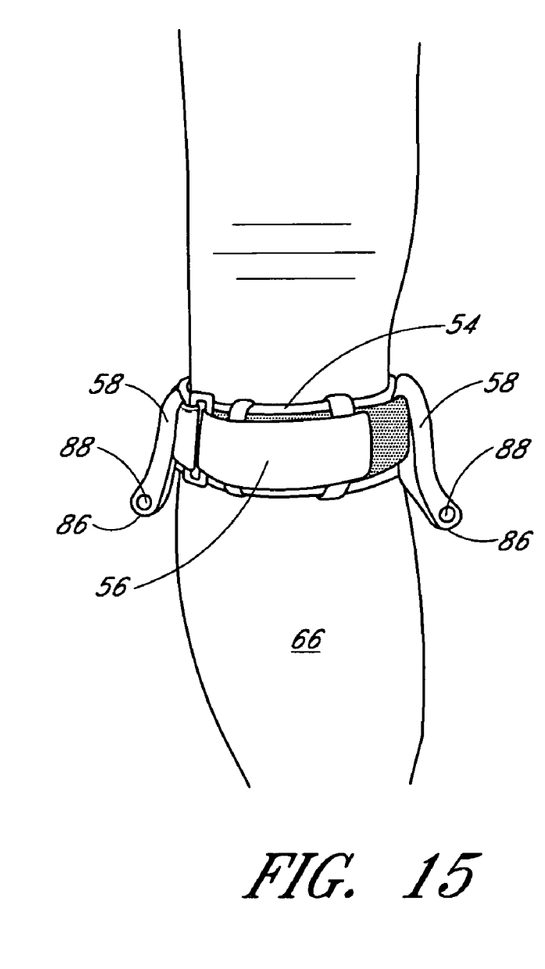
FIG. 15 is a rear elevational view of the inner band, leg, outer belt and suspenders of FIG. 14.

With reference to FIGS. 14 and 15, a pair of suspenders 58 is releasably securable to the outer belt 56. Each suspender 58 comprises an elongate strip of material having first and second ends 86 that are joined to one another so that the strip forms a loop. The suspenders 58 may be constructed of any suitable material, including elastic and inelastic materials. Each looped suspender 58 receives the belt 56. The wearer may, for example, thread the belt 56 through each suspender 58 at the same time that he or she secures the belt 56 about the inner band 54. The suspenders 58 are preferably positioned medially and laterally with respect to the wearer's knee 68 (FIG. 14).

The ends 86 of each suspender 58 preferably include attachment apparatus 88 that is adapted to engage attachment apparatus 90 (FIG. 5) on the rigid frame 60 of a brace 92. For example, the attachment apparatus 88, 90 could comprise mating portions of metal snaps, a button and a loop or threaded fasteners. Alternatively, the ends of each suspender 58 could be permanently attached to the brace 92, as with rivets or adhesive, for example.

With reference to FIGS. 5 and 6, the fully assembled brace suspension system includes the inner band 54, the outer belt 56, the suspenders 58 and the rigid brace frame 60. The inner band 54 wraps around the wearer's leg 66 and provides a comfortable, padded interface for the wearer. The elasticity in the inner band 54 allows it to snugly engage the entire circumference of the leg 66. The outer belt 56, which is preferably inelastic, tightens the grip of the inner band 54 around the leg 66, lessening the chance that the inner band 54 might migrate up or down the leg 66. The loops 74 on the band 54 keep the belt 56 from slipping out of place with respect to the band 54.

The suspenders 58 link the brace frame 60 to the belt 56. They loop around the belt 56 and connect to the frame 60 at a location just below the belt 56. The suspenders 58 are able to swing in the anterior-posterior direction. This arrangement allows vertical force to be transferred through the suspenders 58 to support the brace 92, but does not allow anterior-posterior forces to be transferred between the band 54 and the frame 60.

The band 54 and belt 56 are positioned above the girth of the wearer's gastroc muscle 70. Neither the band 54 nor the belt 56 attaches directly to the brace frame 60. Instead the brace 92 is suspended from the band 54 and the belt 56. The band 54 and belt 56 are advantageously able to remain snug against the wearer's leg 66 while preventing any anterior-posterior forces from being transmitted through the band 54.

Figure 16:
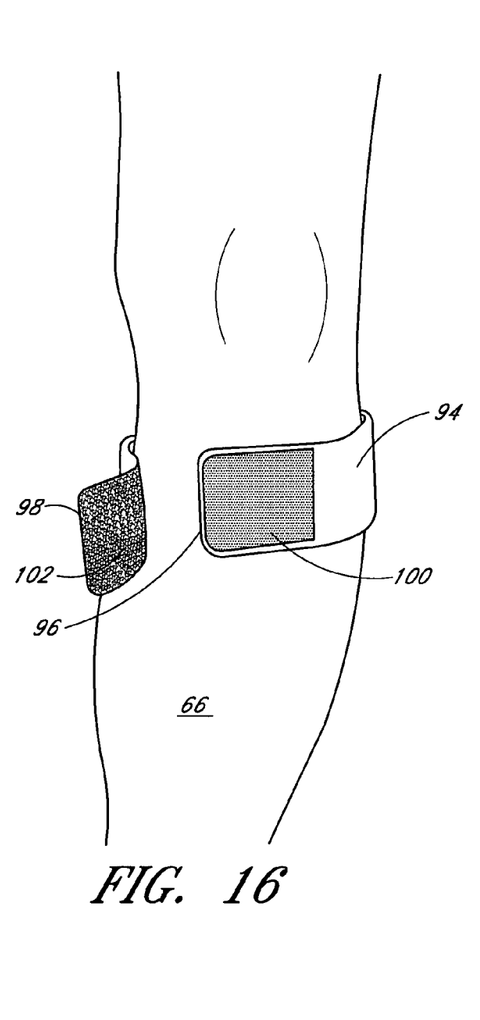
FIG. 16 is a front elevational view of another embodiment of a band for use in the present orthopedic brace suspension system, showing the band secured to a wearer's leg.
Figure 17:
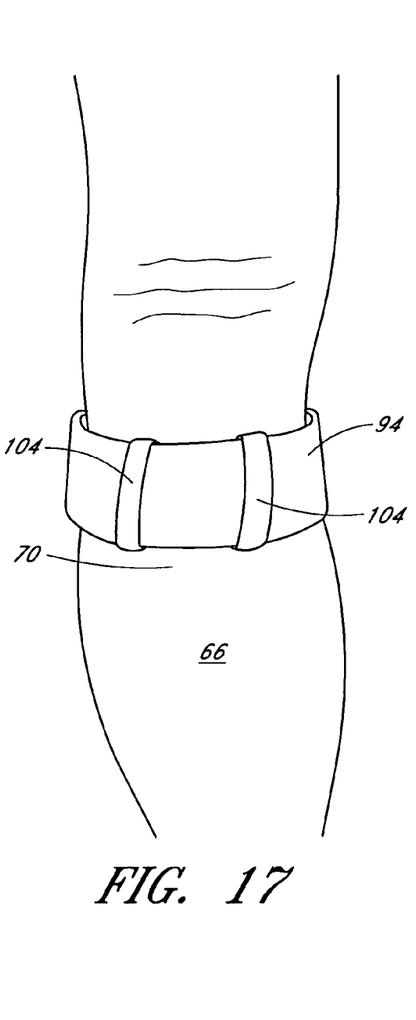
FIG. 17 is a rear elevational view of the band and the leg of FIG. 16.
Figure 18:
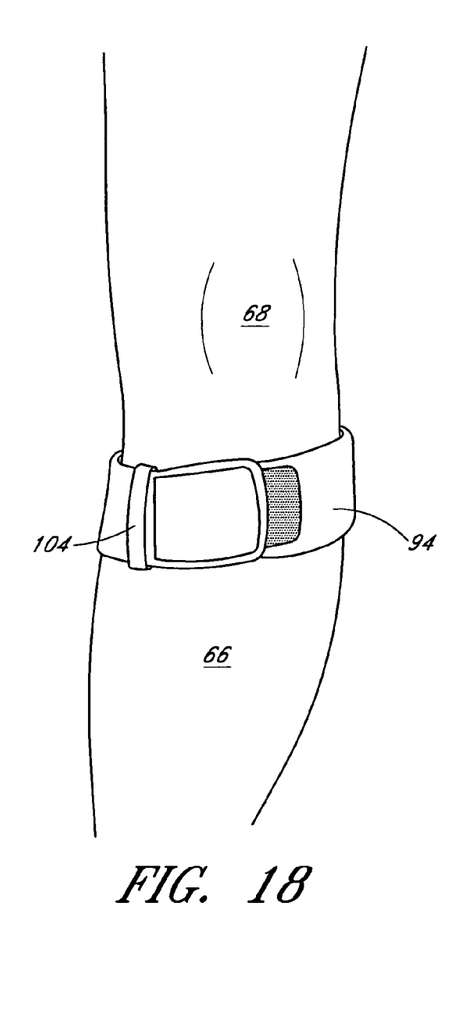
FIG. 18 is a front elevational view of the band and the leg of FIG. 16.

FIGS. 16-18 illustrate another embodiment of the present brace suspension system. This embodiment includes a band 94 that comprises an elongate strip of material including a first end 96 and a second end 98 (FIG. 16). The band 94 extends around the entire circumference of the wearer's leg 66 just below the patella 68 (FIG. 18), and just above the gastroc muscle 70 (FIG. 17). The band 94 is preferably constructed of an inelastic material that is comfortable to wear directly against the skin. Of course, as those of skill in the art will appreciate, the wearer need not wear the band 94 directly against his or her skin, and could, for example, fasten the band 94 over a layer of clothing. Those of skill in the art will further appreciate that the band 94 need not include first and second ends 96, 98. The band 94 could, for example, comprise a continuous loop that the wearer positions on his or her leg by sliding it up and over the foot and ankle.

The first and second ends 96, 98 of the band 94 meet beneath the wearer's patella 68 (FIGS. 16 and 18). The ends 96, 98 preferably include mating fasteners 100, 102, such as hook-and-loop material. Those of skill in the art will appreciate that other types of fasteners, such as buttons or snaps, could be used instead. The wearer secures the band 94 to his or her leg 66 by positioning the first end 96 beneath the patella 68 with the fastener 100 facing out (FIG. 16). The wearer then wraps the second end 98 around the back of his or her leg 66 and secures the fastener 102 on the second end 98 to the mating fastener 100 on the first end 96. Of course, the first and second ends 96, 98 of the band 94 need not be positioned anteriorly of the wearer. The band 94 could be rotated about the wearer's leg 66 so that the first and second ends 96, 98 are positioned anywhere around the leg 66. The band 94 preferably fits snug, but not so tight as to restrict circulation. The band 94 advantageously contacts the entire circumference of the wearer's leg 66. The adjustability of the band 94 also advantageously allows the band 94 to fit a range of leg circumferences without bunching up.

The band 94 includes a plurality of loops 104 that extend in a transverse direction across the band 94. In the illustrated embodiment, the band 94 includes three such loops 104, with one loop 104 being positioned on an anterior portion of the band 94 (FIG. 18), and two loops 104 being positioned on a posterior portion of the band 94 (FIG. 17). Those of skill in the art will appreciate that the band 94 could include virtually any number of loops 104, and that they could be positioned anywhere on the band 94. The loops 104 are preferably secured in place on the band 94, for example with stitching (not shown), such that they cannot slide along the length of the band 94. The loops 104 could, however, be freely slidable along the length of the band 94.

Figure 19:
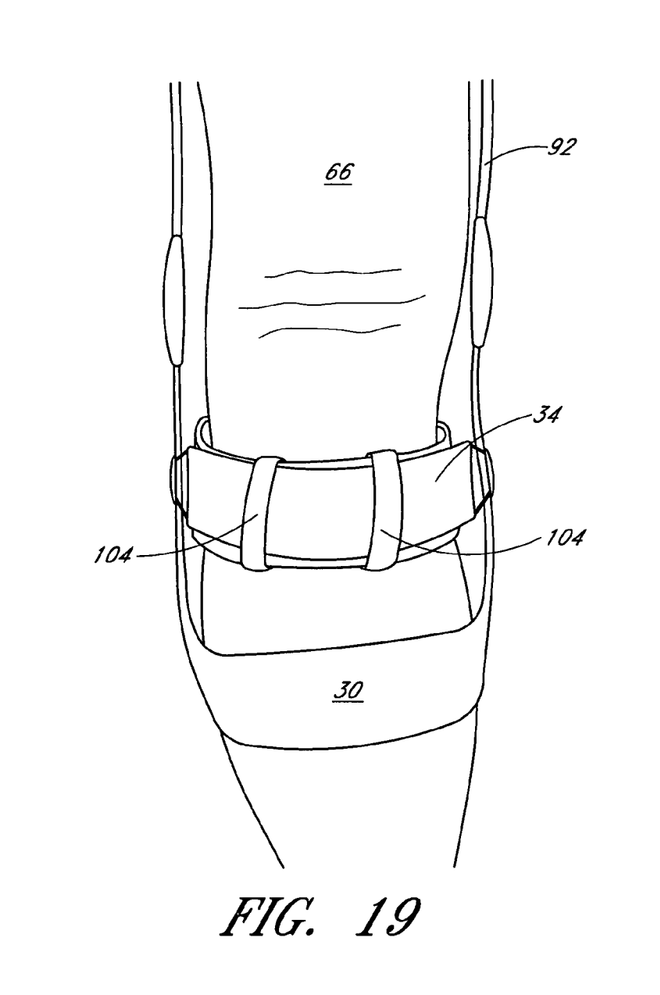
FIG. 19 is a rear elevational view of a brace and the band and the leg of FIG. 16.
Figure 20:
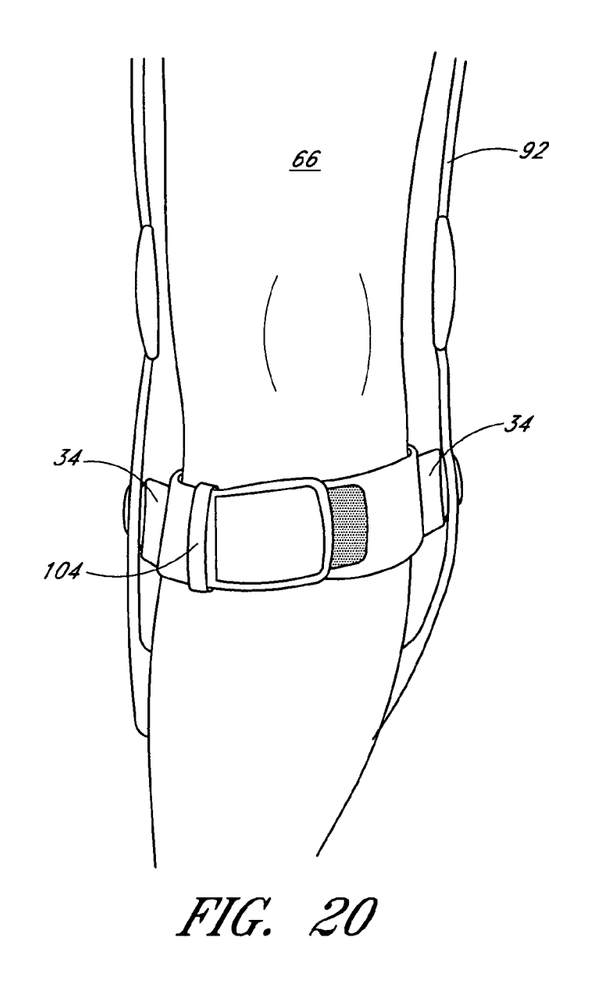
FIG. 20 is a front elevational view of the brace, the band and the leg of FIG. 19.

With reference to FIGS. 19 and 20, the loops 104 are adapted to receive and retain a strap 34 of the knee brace 92, which is threaded through the loops 104. For example, the posterior loops 104 may receive the strap 34 of the brace 30 in FIG. 1 that sits atop the wearer's gastroc muscle 52. If the brace 92 includes an anterior strap 34 that extends across the wearer's leg 66 just below the patella 68, then the anterior belt loop 104 may receive that strap 34. The band 94 thus anchors the brace 92 to the wearer's leg 66, while maintaining contact between the band 94 and the wearer's leg 66 around the entire circumference of the leg 66.

SCOPE OF THE INVENTION

The above presents a description of the best mode contemplated for carrying out the present orthopedic brace suspension system, and of the manner and process of making and using it, in such full, clear, concise, and exact terms as to enable any person skilled in the art to which it pertains to make and use this system. This system is, however, susceptible to modifications and alternate constructions from that discussed above that are fully equivalent. Consequently, this system is not limited to the particular embodiments disclosed. On the contrary, this system covers all modifications and alternate constructions coming within the spirit and scope of the system as generally expressed by the following claims, which particularly point out and distinctly claim the subject matter of the system.

What is claimed is:

1. An orthopedic brace suspension system, comprising:
an orthopedic brace including first and second rigid uprights;
a band that is adapted to extend around a limb of a wearer such that the band contacts substantially the entire circumference of the limb;
a belt that is adapted to extend around the wearer and overlapping the band; and
at least one loop engaged to the band; and
wherein when the brace is worn the band and the belt thread through the at least one loop.

2. The orthopedic brace suspension system of claim 1, further comprising at least one suspender.

3. The orthopedic brace suspension system of claim 1, comprising a belt overlapping the band, wherein the belt is positioned between the band and the inner surface of at least one of first and second rigid uprights.

4. The orthopedic brace suspension system of claim 1, wherein the loop is slidable along the length of the band.

5. An orthopedic brace suspension system, comprising:
an orthopedic brace including first and second rigid uprights; and
a band that is adapted to extend around a limb of a wearer such that the band contacts substantially the entire circumference of the limb and such that the band is closer to the limb of the wearer than the first and second rigid uprights of the brace;
wherein when the brace is worn the an inner surface of the brace is operably connected to an outer surface of the band;
further comprising a belt that is adapted to extend around the wearer, overlapping the band;
further comprising at least one suspender;
wherein the at least one suspender is substantially loop-shaped and receives the belt and attaches to one of the first and second rigid uprights.

6. An orthopedic brace suspension system, comprising:
an orthopedic brace including first and second rigid uprights;
a band that is adapted to extend entirely around a circumference of a body location of the wearer, the band including at least one loop that extends transversely across the band;
a belt that is adapted to extend around the wearer, overlapping the band and threading through the at least one loop; and
at least one suspender extending generally inwardly from one of the first and second uprights;
wherein when the brace is worn the at least one suspender operably connects the belt to one of the first and second rigid uprights; and
wherein the at least one suspender is substantially loop-shaped and receives the belt and attaches to one of the first and second rigid uprights.

7. The orthopedic brace suspension system of claim 6, further comprising at least a second suspender.

8. The orthopedic brace suspension system of claim 6, wherein the band comprises an elastic material.

9. The orthopedic brace suspension system of claim 6, wherein the belt comprises a substantially inelastic material.

10. The orthopedic brace suspension system of claim 6, wherein the band comprises a strip of material having ends, and the ends are releasably securable to one another.

11. The orthopedic brace suspension system of claim 6, wherein the belt includes a D-ring attached to a first end thereof.

12. The orthopedic brace suspension system of claim 11, wherein a second end of the belt threads through the D-ring and folds back over onto an intermediate portion of the belt.

13. The orthopedic brace suspension system of claim 12, wherein the second end includes a hook material or a loop material, and the intermediate portion includes a hook material or a loop material.

14. An orthopedic brace suspension system, comprising:
an orthopedic brace including first and second rigid uprights;
a band that is adapted to extend entirely around a circumference of a body location of the wearer, the band including at least one loop that extends transversely across the band; and
a belt that is adapted to extend around the wearer, overlapping the band and threading through the at least one loop; and
at least one suspender extending generally inwardly from one of the first and second uprights;
wherein when the brace is worn the at least one suspender operably connects the belt to one of the first and second rigid uprights;
wherein the at least one suspender comprises a substantially elastic material.

* * * * *